(12) United States Patent
Echelard et al.

(10) Patent No.: US 6,580,017 B1
(45) Date of Patent: Jun. 17, 2003

(54) METHODS OF RECONSTRUCTED GOAT EMBRYO TRANSFER

(75) Inventors: Yann Echelard, Jamaica Plains, MA (US); Esmail Behbodi, Shrewsbury, MA (US); William Gavin, Dudley, MA (US); David Melican, Fiskdale, MA (US)

(73) Assignee: Genzyme Transgenics Corporation, Framingham, MA (US)

( * ) Notice: Subject to any disclaimer, the term of this patent is extended or adjusted under 35 U.S.C. 154(b) by 0 days.

(21) Appl. No.: 09/298,971

(22) Filed: Apr. 23, 1999

Related U.S. Application Data
(60) Provisional application No. 60/106,728, filed on Nov. 2, 1998.

(51) Int. Cl.$^7$ .......................... C12N 15/00; A01K 67/00

(52) U.S. Cl. ............................... 800/24; 800/8; 800/14

(58) Field of Search ........................... 800/24, 7, 8, 13

(56) References Cited

U.S. PATENT DOCUMENTS 5,945,577 A * 8/1999 Stice et al. .................... 800/24
6,011,197 A * 1/2000 Strelchenko et al. .......... 800/24

FOREIGN PATENT DOCUMENTS

| WO | WO96/26268 | 8/1996 |
| WO | WO97/07669 | 3/1997 |
| WO | WO97/19589 | 6/1997 |

OTHER PUBLICATIONS

Steven L. Stice & Neal L. First, *Progress towards efficient commercial embryo cloning*, Animal Reproduction Science, 33:83–98 (1993) Amsterdam.
Steven L. Stice & James M. Robl, *Nuclear Reprogramming in Nuclear Transplant Rabbit Embryos*, Biology of Reproduction, 39:657–664 (1988).
Philippe Collas & James M. Robl, *Factors Affecting the Efficiency of Nuclear Transplantation in the Rabbit Embryo*, Biology of Reproduction, 43:877–884 (1990).
Burdon, Thomas, G., et al., "Fate of Microinjected Genes in Preimplantation Mouse Embryos", Molecular Reproduction and Development, vol. 33, 1992, pp. 436–442.
Campbell, K.H.S., et al., "Nuclear–Cytoplasmic Interactions during the First Cell Cycle of Nuclear . . . ", Biology of Reproduction, vol. 49, No. 5, Nov. 1993, pp. 933–942.
Collas, Philippe, et al., "Relationship between Nuclear Remodeling and Development in Nuclear Transplant Rabbit Embryos", Biology of Reproduction, vol. 45, No. 3, Sep. 1991, pp. 455–465.
Collas, Philippe, et al., "Effect of Donor Cell Cycle Stage on Chromatin and Spindle Morphology in Nuclear Transplant Rabbit Embryos", Biology of Reproduction, vol. 46, No. 2, Feb. 1992, pp. 501–511.

Collas, Philippe, et al., "Inactivation of Histone H1 Kinase by $Ca^{2+}$ in Rabbit Oocytes", Molecular Reproduction and Development, vol. 40, No. 2, Feb. 1995, pp. 253–258.
Pinto–Correia, Clara, et al., "Chromatin and Microtubule Organization in the First Cell Cycle in Rabbit . . . ", Molecular Reproduction and Development, vol. 23, No. 1, Jan. 1993, pp. 33–42.
Ebert, K.M., et al., "Transgenic Farm Animals", Theriogenology, vol. 39, No. 1, Jan. 1993, pp. 121–135.
Ebert, Karl, M., et al., "Transgenic Production of a Variant of Human Tissue–Type Plasminogen Activator . . . ", Bio/Technology, vol. 9, Sep. 1991, pp. 835–838.
Echelard, Yann, "Recombinant Protein Production in Transgenic Animals", Current Opinion in Biotechnology, vol. 7, 1996, pp. 536–540.
Garry, E.B., et al., "Postnatal Characteristics of Calves Produced by Nuclear Transfer Cloning", Theriogenology, vol. 45, No. 1, Jan. 1, 1996, pp. 141–152.
Kono, T., et al., "Effect of Ooplast Activation on the Development of Oocytes Following Nucleus Transfer in Cattle", Theriogenology, vol. 41, No. 7, 1994, pp. 1463–1471.
Kroemer, Guido, et al., "The Biochemistry of Programmed Cell Death", The FASEB Journal, vol. 9, No. 13, Oct. 1995, pp. 1277–1287.
Murray, Andrew, W., et al., "The Role of Cyclin Synthesis and Degradation in the Control of Maturation Promoting Factor Activity", Nature, vol. 339, No. 6222, May 25, 1989, pp. 280–286.
Nurse, Paul, "Universal Control Mechanism Regulating Onset of M–Phase", Nature, vol. 344, No. 6266, Apr. 5, 1990, pp. 503–508.
Parrish, J.J., et al., "Current Concepts of Cell–Cycle Regulation and its Relationship to Oocyte Maturation, Fertilization and Embryo Development", Theriogenology, vol. 38, No. 1, Jul. 1992, pp. 277–296.
Sagata, Noriyuki, et al., "The C–Mos Proto–Oncogene Product is a Cytostatic Factor Responsible for Meiotic Arrest in Vertebrate Eggs", Nature, vol. 342, No. 6249, Nov. 30, 1989, pp. 512–518.
Schnieke, Angelika, E., et al., "Human Factor IX Transgenic Sheep Produced by Transfer of Nuclei from Transfected Fetal Fibroblasts", Science, vol. 278, Dec. 19, 1997, pp. 2021–2192.
Smith, L.C., et al., "Influence of Cell Cycle Stage at Nuclear Transplantation on the Development in vitro of Mouse Embryos", Journal of Reproduction & Fertility, vol. 84, No. 2, Nov. 1988, pp. 619–624.

(List continued on next page.)

Primary Examiner—Deborah Crouch
(74) Attorney, Agent, or Firm—Fish & Richardson, P.C.

(57) ABSTRACT

The invention features methods of producing a mammal, e.g., a cloned or transgenic mammal. The method includes maintaining a reconstructed embryo in culture until the embryo is in the 2 to 8 cell stage of embryogenesis, transferring the embryo at the 2 to 8 cell stage into a recipient mammal, and allowing the embryo to develop into a mammal.

73 Claims, No Drawings

OTHER PUBLICATIONS

Stice, Steven, L., et al., "Multiple Generational Bovine Embryo Cloning", Biology of Reproduction, vol. 48, No. 4, Apr. 1993, pp. 715–719.

Stice, Steven, L., et al., "Bovine Nuclear Transfer Embryos: Oocyte Activation Prior to Blastomere Fusion", Molecular Reproduction and Development, vol. 38, No. 1, May 1994, pp. 61–68.

Wakayama, T., et al., "Full–Term Development of Mice from Enucleated Oocytes Injected with Cumulus Cell Nuclei", Nature, vol. 394, Jul. 23, 1998, pp. 369–374.

Wall, R.J., "Transgenic Livestock: Progress and Prospects for the Future", Theriogenology, vol. 45, No. 1, Jan. 1, 1996, pp. 57–68.

Wells, David, N., et al., "Production of Cloned Lambs from an Established Embryonic Cell Line: A Comparison Between . . . ", Biology of Reproduction, vol. 57, No. 2, Aug. 1997, pp. 385–393.

Whitaker, Michael, et al., "Calcium and Cell Cycle Control", Development, vol. 108(4), Apr. 1990, pp. 525–542.

Wilmut, I., et al., "Viable Offspring Derived from Fetal and adult Mammalian Cells", Nature, vol. 385, Feb. 27, 1997, pp. 810–813.

Wilson, J.M., et al., "Comparison of Birth Weight and Growth Characteristics of Bovine Calves Produced by Nuclear Transfer (Cloning) . . . " Animal Reproduction Science, vol. 38, Nos. 1, 2, Mar. 1995, pp. 73–83.

Young, Michael, W., et al., "Production of Biopharmaceutical Proteins in the Milk of Transgenic Dairy Animals", Biopharm, Jun. 1997, pp. 34–38.

Bordignon, Vilceu and Lawrence C. Smith, "Telophase Enucleation: An improved method to prepare recipient cytoplasts for use in bovine nuclear transfer", Molecular Reproduction And Development, 49:29–36, 1998.

Gootwine, E. et al., "Factors affecting success of embryo collection and transfer in a transgenic goat program", Theriogenology, 48 (3): 485–499, 1997.

Lewis–Williams, J. et al., "Birth of successfully identified transgenic goats using preimplantation stage embyos biopsied for fish", Theriogenology, 47 (1): 226–226, 1997.

\* cited by examiner

METHODS OF RECONSTRUCTED GOAT EMBRYO TRANSFER

CROSS REFERENCE TO RELATED APPLICATIONS

Under 35 USC §119(e) (1), this application claims the benefit of prior U.S. provisional application serial No. 60/106,728, filed Nov. 2, 1998.

BACKGROUND OF THE INVENTION

Recently, developments in the area of cloning and cloning procedures have expanded. For example, there have been several reports of live births of animals using cloning procedures. Live lambs were produced following nuclear transfer of cultured embryonic disc cells. Campbell et al. (1996) *Nature* 380:64–68. Campbell et al. disclose methods of transferring the nucleus of a quiescent cell into an enucleated oocyte to form a reconstructed embryo. The reconstructed embryo was developed until the morula to blastocyst stage in vivo prior to transfer into a recipient female.

Other reports of the live births of cloned mammals have also relied upon the transfer of a reconstructed embryo after it has reached the blastocyst stage of embryogenesis.

SUMMARY OF THE INVENTION

The present invention is based, in part, on the discovery that a reconstructed embryo which is transferred into a recipient mammal at the two to four cell stage of embryogenesis can develop into a cloned mammal. The mammal can be an embryo, a fetus, or a post natal mammal, e.g., an adult mammal.

Accordingly, in one aspect, the invention features a method of producing a non-human mammal, e.g., a cloned mammal, e.g., a goat, cow, pig, horse, sheep, llama, camel. The method includes maintaining a mammalian reconstructed embryo, e.g., a reconstructed embryo wherein the genome is derived from a somatic cell, in culture until the embryo is in the 2 to 8 cell stage, transferring the embryo at the 2 to 8 cell stage into a recipient mammal, and allowing the reconstructed embryo to develop into a mammal, to thereby produce a mammal.

In a preferred embodiment, the mammal develops from the reconstructed embryo. In another embodiment, the mammal is a descendant of a mammal which developed from the reconstructed embryo.

In a preferred embodiment, the reconstructed embryo is maintained in culture until the embryo is in the 2 to 8, the 2 to 6, the 2 to 4 cell stage of embryogenesis.

In a preferred embodiment, the genome of the reconstructed embryo is derived from: a somatic cell, e.g., a fibroblast or epithelial cell; a genetically engineered somatic cell, e.g., a somatic cell comprising a transgenic sequence.

In a preferred embodiment, the method further includes mating the mammal which develops from the reconstructed embryo with: a second mammal; a second mammal which develops from a reconstructed embryo or is descended from a mammal which developed from a reconstructed embryo; or a second mammal developed from a reconstructed embryo, or descended from a mammal which developed from a reconstructed embryo, which was formed from genetic material from the same animal, an animal of the same genotype, or same cell line, which supplied the genetic material for the first mammal. In a preferred embodiment, a first transgenic mammal which develops from the reconstructed embryo can be mated with a second transgenic mammal which developed from a reconstructed embryo and which contains a different transgene that the first transgenic mammal.

In a preferred embodiment, the mammal is a male mammal. In other preferred embodiments, the mammal is a female mammal. A female mammal can be induced to lactate and milk can be obtained from the mammal.

In a preferred embodiment: a product, e.g., a protein, e.g., a recombinant protein, e.g., a human protein, is recovered from the mammal; a product, e.g., a protein, e.g., a human protein, is recovered from the milk, urine, hair, blood, skin or meat of the mammal.

In a preferred embodiment, the mammal is: embryonic; fetal; or, postnatal, e.g., adult.

In a preferred embodiment, the genome of the reconstructed embryo is derived from a genetically engineered somatic cell, e.g., a transgenic cell or a cell which a nucleic acid has been introduced.

In another aspect, the invention features a method of producing a non-human mammal, e.g., a transgenic mammal, e.g., a goat, cow, pig, horse, sheep, llama, camel. The method includes maintaining a mammalian reconstructed embryo (e.g., a reconstructed embryo wherein its genome is derived from a genetically engineered somatic cell) in culture until the embryo is in the 2 to 8 cell stage, transferring the embryo at the 2 to 8 cell stage into a recipient mammal, and allowing the reconstructed embryo to develop into a mammal, to thereby produce a transgenic mammal.

In a preferred embodiment, the mammal develops from the reconstructed embryo. In another embodiment, the mammal is a descendant of a mammal which developed from the reconstructed embryo.

In a preferred embodiment, the reconstructed embryo is maintained in culture until the embryo is in the 2 to 8, the 2 to 6, the 2 to 4 cell stage of embryogenesis.

In a preferred embodiment, the method further includes mating the mammal which develops from the reconstructed embryo with: a second mammal; a second mammal which develops from a reconstructed embryo or is descended from a mammal which developed from a reconstructed embryo; or a second mammal developed from a reconstructed embryo, or descended from a mammal which developed from a reconstructed embryo, which was formed from genetic material from the same animal, an animal of the same genotype, or same cell line, which supplied the genetic material for the first mammal. In a preferred embodiment, a first transgenic mammal which develops from the reconstructed embryo can be mated with a second transgenic mammal which developed from a reconstructed embryo and which contains a different transgene that the first transgenic mammal.

In a preferred embodiment, the mammal is a male mammal. In other preferred embodiments, the mammal is a female mammal. A female mammal can be induced to lactate and milk can be obtained from the mammal.

In a preferred embodiment: a product, e.g., a protein, e.g., a recombinant protein, e.g., a human protein, is recovered from the mammal; a product, e.g., a protein, e.g., a human protein, is recovered from the milk, urine, hair, blood, skin or meat of the mammal.

In a preferred embodiment, the genome of the genetically engineered somatic cell includes a transgenic sequence. The transgenic sequence can be any of: a heterologous transgene, e.g., a human transgene; a knockout, knockin or other event which disrupts the expression of a mammalian gene; a sequence which encodes a protein, e.g., a human protein; a heterologous promoter; a heterologous sequence under the control of a promoter, e.g., a caprine promoter. The transgenic sequence can encode any product of interest such as a protein, polypeptide or peptide.

In a preferred embodiment, the transgenic sequence encodes any of: a hormone, an immunoglobulin, a plasma protein, and an enzyme. The transgenic sequence can encode any protein whose expression in the transgenic mammal is desired, e.g., any of: α-1 proteinase inhibitor, alkaline phosphotase, angiogenin, extracellular superoxide dismutase, fibrogen, glucocerebrosidase, glutamate decarboxylase, human serum albumin, myelin basic protein, proinsulin, soluble CD4, lactoferrin, lactoglobulin, lysozyme, lactoalbumin, erythrpoietin, tissue plasminogen activator, human growth factor, antithrombin III, insulin, prolactin, and (α1-antitrypsin.

In a preferred embodiment, the transgenic sequence encodes a human protein.

In a preferred embodiment, the transgenic sequence is under the control of a promoter, e.g., a caprine or heterologous promoter. The promoter can be a tissue-specific promoter. The tissue specific promoter can be any of: milk-specific promoters; blood-specific promoters; muscle-specific promoters; neural-specific promoters; skin-specific promoters; hair-specific promoters; and urine-specific promoters. The milk-specific promoter can be, e.g., any of: a casein promoter, a beta lactoglobulin promoter, a whey acid protein promoter and a lactalbumin promoter.

In a preferred embodiment, a nucleic acid can be introduced into the genome of the genetically engineered somatic cell. The nucleic acid can be any of: a heterologous transgene, e.g., a human transgene; a knockout, knockin or other event which disrupts the expression of a mammalian gene; a sequence which encodes a protein, e.g., a human protein; a heterologous promoter; a heterologous sequence under the control of a promoter, e.g., a caprine or heterologous promoter. The nucleic acid sequence can encode any product of interest such as a protein, polypeptide or peptide.

In a preferred embodiment, the nucleic acid encodes any of: a hormone, an immunoglobulin, a plasma protein, and an enzyme. The nucleic acid sequence can encode any protein whose expression in the transgenic mammal is desired, e.g., any of: α-1 proteinase inhibitor, alkaline phosphotase, angiogenin, extracellular superoxide dismutase, fibrogen, glucocerebrosidase, glutamate decarboxylase, human serum albumin, myelin basic protein, proinsulin, soluble CD4, lactoferrin, lactoglobulin, lysozyme, lactoalbumin, erythrpoietin, tissue plasminogen activator, human growth factor, antithrombin III, insulin, prolactin, and α1-antitrypsin.

In a preferred embodiment, the nucleic acid sequence encodes a human protein.

In a preferred embodiment, the nucleic acid sequence is under the control of a promoter, e.g., a caprine or heterologous promoter. The promoter can be a tissue-specific promoter. The tissue specific promoter can be any of: milk-specific promoters; blood-specific promoters; muscle-specific promoters; neural-specific promoters; skin-specific promoters; hair-specific promoters; and urine-specific promoters. The milk-specific promoter can be, e.g., any of: a casein promoter, a beta lactoglobulin promoter, a whey acid protein promoter and a lactalbumin promoter.

In another aspect, the invention features a method of producing a cloned goat. The method includes maintaining a caprine reconstructed embryo (e.g., a reconstructed embryo wherein its genome is derived from a caprine somatic cell) in culture until the embryo is in the 2 to 8 cell stage, transferring the embryo at the 2 to 8 cell stage into a recipient goat, and allowing the reconstructed embryo to develop into a goat, to thereby produce a goat.

In a preferred embodiment, the goat is: embryonic; fetal; or, postnatal, e.g., adult.

In a preferred embodiment, the goat develops from the reconstructed embryo. In another embodiment, the goat is a descendant of a goat which developed from the reconstructed embryo.

In a preferred embodiment, the reconstructed embryo is maintained in culture until the embryo is in the 2 to 8, the 2 to 6, the 2 to 4 cell stage of embryogenesis.

In a preferred embodiment, the genome of the reconstructed embryo is derived from: a caprine somatic cell, e.g., a fibroblast or epithelial cell; a genetically engineered caprine somatic cell, e.g., the genome of the caprine somatic cell comprises a transgenic sequence or a nucleic acid has been introduced into the genome of the somatic cell.

In a preferred embodiment, the method further includes mating the goat which develops from the reconstructed embryo with: a second goat; a second goat which develops from a reconstructed embryo or is descended from a goat which developed from a reconstructed embryo; or a second goat developed from a reconstructed embryo, or descended from a goat which developed from a reconstructed embryo, which was formed from genetic material from the same animal, an animal of the same genotype, or same cell line, which supplied the genetic material for the first goat. In a preferred embodiment, a first transgenic goat which develops from the reconstructed embryo can be mated with a second transgenic goat which developed from a reconstructed embryo and which contains a different transgene that the first transgenic goat.

In a preferred embodiment, the goat is a male goat. In other preferred embodiments, the goat is a female goat. A female goat can be induced to lactate and milk can be obtained from the goat.

In a preferred embodiment: a product, e.g., a protein, e.g., a recombinant protein, e.g., a human protein, is recovered from the goat; a product, e.g., a protein, e.g., a human protein, is recovered from the milk, urine, hair, blood, skin or meat of the goat.

In another aspect, the invention features a method of producing a transgenic goat. The method includes maintaining a caprine reconstructed embryo (e.g., a reconstructed embryo wherein its genome is derived from a genetically engineered somatic cell) in culture until the embryo is in the 2 to 8 cell stage, transferring the embryo at the 2 to 8 a cell stage into a recipient goat, and allowing the reconstructed embryo to develop into a goat, to thereby produce a transgenic goat.

In a preferred embodiment, the goat is: embryonic; fetal; or, postnatal, e.g., adult.

In a preferred embodiment, the goat develops from the reconstructed embryo. In another embodiment, the goat is a descendant of a goat which developed from the reconstructed embryo.

In a preferred embodiment, the reconstructed embryo is maintained in culture until the embryo is in the 2 to 8, the 2 to 6, the 2 to 4 cell stage of embryogenesis.

In a preferred embodiment, the genome of the reconstructed embryo is derived from a somatic cell, e.g., a fibroblast or epithelial cell.

In a preferred embodiment, the method further includes mating the goat which develops from the reconstructed embryo with: a second goat; a second goat which develops from a reconstructed embryo or is descended from a goat which developed from a reconstructed embryo; or a second goat developed from a reconstructed embryo, or descended from a goat which developed from a reconstructed embryo, which was formed from genetic material from the same animal, an animal of the same genotype, or same cell line, which supplied the genetic material for the first goat. In a preferred embodiment, a first transgenic goat which develops from the reconstructed embryo can be mated with a second transgenic goat which developed from a reconstructed embryo and which contains a different transgene that the first transgenic goat.

In a preferred embodiment, the goat is a male goat. In other preferred embodiments, the goat is a female goat. A female goat can be induced to lactate and milk can be obtained from the goat.

In a preferred embodiment: a product, e.g., a protein, e.g., a recombinant protein, e.g., a human protein, is recovered from the goat; a product, e.g., a protein, e.g., a human protein, is recovered from the milk, urine, hair, blood, skin or meat of the goat.

In a preferred embodiment, the genome of the genetically engineered somatic cell includes a transgenic sequence. The transgenic sequence can be any of: a heterologous transgene, e.g., a human transgene; a knockout, knockin or other event which disrupts the expression of a mammalian gene; a sequence which encodes a protein, e.g., a human protein; a heterologous promoter; a heterologous sequence under the control of a promoter, e.g., a caprine or heterologous promoter. The transgenic sequence can encode any product of interest such as a protein, polypeptide or peptide.

In a preferred embodiment, the transgenic sequence encodes any of: a hormone, an immunoglobulin, a plasma protein, and an enzyme. The transgenic sequence can encode any protein whose expression in the transgenic mammal is desired, e.g., any of: α-1 proteinase inhibitor, alkaline phosphotase, angiogenin, extracellular superoxide dismutase, fibrogen, glucocerebrosidase, glutamate decarboxylase, human serum albumin, myelin basic protein, proinsulin, soluble CD4, lactoferrin, lactoglobulin, lysozyme, lactoalbumin, erythrpoietin, tissue plasminogen activator, human growth factor, antithrombin III, insulin, prolactin, and α1-antitrypsin.

In a preferred embodiment, the transgenic sequence encodes a human protein.

In a preferred embodiment, the transgenic sequence is under the control of a promoter, e.g., a caprine or heterologous promoter. The promoter can be a tissue-specific promoter. The tissue specific promoter can be any of: milk-specific promoters; blood-specific promoters; muscle-specific promoters; neural-specific promoters; skin-specific promoters; hair-specific promoters; and urine-specific promoters. The milk-specific promoter can be, e.g., any of: a casein promoter, a beta lactoglobulin promoter, a whey acid protein promoter and a lactalbumin promoter.

In a preferred embodiment, a nucleic acid has been introduced into the genome of the genetically engineered somatic cell. The nucleic acid sequence can be any of: a heterologous transgene, e.g., a human transgene; a knockout, knockin or other event which disrupts the expression of a mammalian gene; a sequence which encodes a protein, e.g., a human protein; a heterologous promoter; a heterologous sequence under the control of a promoter, e.g., a caprine or heterologous promoter. The transgenic sequence can encode any product of interest such as a protein, polypeptide or peptide.

In a preferred embodiment, the nucleic acid encodes any of: a hormone, an immunoglobulin, a plasma protein, and an enzyme. The nucleic acid sequence can encode any protein whose expression in the transgenic mammal is desired, e.g., any of: α-1 proteinase inhibitor, alkaline phosphotase, angiogenin, extracellular superoxide dismutase, fibrogen, glucocerebrosidase, glutamate decarboxylase, human serum albumin, myelin basic protein, proinsulin, soluble CD4, lactoferrin, lactoglobulin, lysozyme, lactoalbumin, erythrpoietin, tissue plasminogen activator, human growth factor, antithrombin III, insulin, prolactin, and α1-antitrypsin.

In a preferred embodiment, the nucleic acid sequence encodes a human protein.

In a preferred embodiment, the nucleic acid sequence is under the control of a promoter, e.g., a caprine or heterologous promoter. The promoter can be a tissue-specific promoter. The tissue specific promoter can be any of: milk-specific promoters; blood-specific promoters; muscle-specific promoters; neural-specific promoters; skin-specific promoters; hair-specific promoters; and urine-specific promoters. The milk-specific promoter can be, e.g., any of: a casein promoter, a beta lactoglobulin promoter, a whey acid protein promoter and a lactalbumin promoter.

In another aspect, the invention features a kit. The kit includes a reconstructed embryo which is in the 2 to 8 cell stage. In a preferred embodiment, the kit further includes instructions for producing a mammal, e.g., an embryonic, fetal or postnatal mammal.

In another aspect, the invention features a kit which includes a later stage embryo, e.g., an embryo after the 8 cell stage, or a fetus, obtained, e.g., by the methods described herein.

The terms protein, polypeptide and peptide are used interchangeably herein.

The phrase "a genome derived from a somatic cell", as used herein, refers to the nuclear transfer of a somatic cell, e.g., the chromosomal genome of a somatic cell, into a functionally enucleated oocyte.

The term "genetically engineered", as used herein, refers to a cell altered by human intervention, e.g., a transgenic cell or other cell into which a nucleic acid has been introduced.

As used herein, the term "transgenic sequence" refers to a nucleic acid sequence (e.g., encoding one or more human proteins), which is inserted by artifice into a cell. The transgenic sequence, also referred to herein as a transgene, can become part of the genome of an animal which develops in whole or in part from that cell. In embodiments of the invention, the transgenic sequence is integrated into the chromosomal genome. If the transgenic sequence is integrated into the genome it results, merely by virtue of its insertion, in a change in the nucleic acid sequence of the genome into which it is inserted. A transgenic sequence can be partly or entirely species-heterologous, i.e., the transgenic sequence, or a portion thereof, can be from a species which is different from the cell into which it is introduced. A transgenic sequence can be partly or entirely species-homologous, i.e., the transgenic sequence, or a portion thereof, can be from the same species as is the cell into which it is introduced. If a transgenic sequence is homologous (in the sequence sense or in the species-homologous sense) to an endogenous gene of the cell into which it is introduced, then the transgenic sequence, preferably, has one or more of the following characteristics: it is designed for insertion, or is inserted, into the cell's genome in such a way as to alter the sequence of the genome of the cell into which it is inserted (e.g., it is inserted at a location which differs from that of the endogenous gene or its insertion results in a change in the sequence of the endogenous endogenous gene); it includes a mutation, e.g., a mutation which results in misexpression of the transgenic sequence; by virtue of its insertion, it can result in misexpression of the gene into which it is inserted, e.g., the insertion can result in a knockout of the gene into which it is inserted. A transgenic sequence can include one or more transcriptional regulatory sequences and any other nucleic acid sequences, such as introns, that may be necessary for a desired level or pattern of expression of a selected nucleic acid, all operably linked to the selected nucleic acid. The transgenic sequence can include an enhancer sequence and or sequences which allow for secretion.

The term "heterologous promoter" as used herein, refers to a promoter which is not normally associated with the gene it controls or which is heterologous to the mammal into which it is introduced.

The terms "reconstructed embryo", "reconstituted embryo" and "nuclear transfer unit" are used interchangeably herein.

Other features and advantages of the invention will be apparent from the following description and from the claims.

DETAILED DESCRIPTION OF THE INVENTION

Donor Cells

Somatic cells can supply the genome for producing a reconstructed embryo in the methods described herein. The term "somatic cell", as used herein, refers to a differentiated cell. The cell can be a somatic cell or a cell that is committed to a somatic cell lineage. Alternatively, any of the methods and animals described herein can utilize a diploid stem cell that gives rise to a germ cell in order to supply the genome for producing a reconstructed embryo.

The somatic cell can be from an animal or from a cell culture. If taken from an animal, the animal can be at any stage of development, e.g., an embryo, a fetus or an adult. Embryonic cells are preferred. Embryonic cells can include embryonic stem cells as well as embryonic cells committed to a somatic cell lineage. Such cells can be obtained from the endoderm, mesoderm or ectoderm of the embryo. Preferably, the embryonic cells are committed to somatic cell lineage. Embryonic cells committed to a somatic cell lineage refer to cells isolated on or after day 10 of embryogenesis. However, cells can be obtained prior to day ten of embryogenesis. If a cell line is used as a source of a chromosomal genome, primary cells are preferred. The term "primary cell line" as used herein includes primary cell lines as well as primary-derived cell lines.

Suitable somatic cells include fibroblasts (e.g., primary fibroblasts, e.g., embryonic primary fibroblasts), muscle cells (e.g., myocytes), cumulus cells, neural cells, and mammary cells. Other suitable cells include hepatocytes and pancreatic islets. Preferably, the somatic cell is an embryonic somatic cell, e.g., a cell isolated on or after day 10 of embryogenesis. The genome of the somatic cells can be the naturally occurring genome, e.g., for the production of cloned mammals, or the genome can be genetically altered to comprise a transgenic sequence, e.g., for the production of transgenic cloned mammals.

Somatic cells can be obtained by, for example, dissociation of tissue, e.g., by mechanical (e.g., chopping, mincing) or enzymatic means (e.g., trypsinization) to obtain a cell suspension and then by culturing the cells until a confluent monolayer is obtained. The somatic cells can then be harvested and prepared for cryopreservation, or maintained as a stock culture. The isolation of caprine somatic cells, e.g., fibroblasts, is described herein.

The somatic cell can be a quiescent or non-quiescent somatic cell. "Non-quiescent", as used herein, refers to a cell in mitotic cell cycle. The mitotic cell cycle has four distinct phases, $G_1$, S, $G_2$ and M. The beginning event in the cell cycle, called START, takes place during the $G_1$ phase. "START" as used herein refers to early $G_1$ stage of the cell cycle prior to the commitment of a cell to proceeding through the cell cycle. For example, 1, 2, 3, 4, 5, 6, 7, 8, 9, 10 up to 11 hours after a cell enters the $G_1$ stage, the cell is considered prior to START. The decision as to whether the cell will undergo another cell cycle is made at START. Once the cell has passed through START, it passes through the remainder of the $G_1$ phase (i.e., the pre-DNA synthesis stage). The S phase is the DNA synthesis stage, which is followed by the $G_2$ phase, the stage between synthesis and mitosis. Mitosis takes place during the M phase. If at START, the cell does not undergo another cell cycle, the cell becomes quiescent. In addition, a cell can be induced to exit the cell cycle and become quiescent. A "quiescent" cell, also referred to as a cell in $G_0$ phase, refers to a cell which is not in any of the four phases of the cell cycle. Preferably, the somatic cell is a cell in the $G_0$ phase or the $G_1$ phase of the mitotic cell cycle.

Using donor somatic cells at certain phases of the cell cycle, e.g., $G_0$ or $G_1$ phase, can allow for synchronization between the oocyte and the genome of the somatic cell. For example, reconstruction of an oocyte in metaphase II by introduction of a nucleus of a somatic cell in $G_0$ or $G_1$, e.g., by simultaneous activation and fusion, can mimic the events occurring during fertilization.

Methods of determining which phase of the cell cycle a cell is in are known. For example, as described below in the Examples, various markers are present at different stages of the cell cycle. Such markers can include cyclins D 1, 2, 3 and proliferating cell nuclear antigen (PCNA) for $G_1$, and BrDu to detect DNA synthetic activity. In addition, cells can be induced to enter the $G_0$ stage by culturing the cells on serum-deprived medium. Alternatively, cells in $G_0$ stage can be induced to enter the cell cycle, i.e., at $G_1$ stage, by serum activation.

Sources of Genetically Engineered Somatic Cells

Transgenic Mammals

Methods for generating non-human transgenic mammals which can be used as a source of somatic cells in the invention are known in the art. Such methods can involve introducing DNA constructs into the germ line of a mammal to make a transgenic mammal. For example, one or several copies of the construct may be incorporated into the genome of a mammalian embryo by standard transgenic techniques.

Although goats are a preferred source of genetically engineered somatic cells, other non-human mammals can be used. Preferred non-human mammals are ruminants, e.g., cows, sheep, camels or goats. Goats of Swiss origin, e.g., the Alpine, Saanen and Toggenburg breed goats, are useful in the methods described herein. Additional examples of preferred non-human animals include oxen, horses, llamas, and pigs. The mammal used as the source of genetically engineered cells will depend on the transgenic mammal to be obtained by the methods of the invention as, by way of example, a goat genome should be introduced into a goat functionally enucleated oocyte.

Preferably, the somatic cells for use in the invention are obtained from a transgenic goat. Methods of producing transgenic goats are known in the art. For example, a transgene can be introduced into the germline of a goat by microinjection as described, for example, in Ebert et al. (1994) Bio/Technology 12:699, hereby incorporated by reference.

Other transgenic non-human animals to be used as a source of genetically engineered somatic cells can be produced by introducing a transgene into the germline of the non-human animal. Embryonal target cells at various developmental stages can be used to introduce transgenes. Different methods are used depending on the stage of development of the embryonal target cell. The specific line(s) of any animal used to practice this invention are selected for general good health, good embryo yields, good pronuclear visibility in the embryo, and good reproductive fitness. In addition, the haplotype is a significant factor.

Transfected Cell Lines

Genetically engineered somatic cells for use in the invention can be obtained from a cell line into which a nucleic acid of interest, e.g., a nucleic acid which encodes a protein, has been introduced.

A construct can be introduced into a cell via conventional transformation or transfection techniques. As used herein, the terms "transfection" and "transformation" include a variety of techniques for introducing a transgenic sequence into a host cell, including calcium phosphate or calcium chloride co-precipitation, DEAE-dextrane-mediated transfection, lipofection, or electroporation. In addition, biological vectors, e.g., viral vectors can be used as described below. Suitable methods for transforming or transfecting host cells can be found in Sambrook et al., *Molecular Cloning: A Laboratory Manuel, $2^{nd}$ ed., Cold Spring Harbor Laboratory,* (Cold Spring Harbor Laboratory Press, Cold Spring Harbor, N.Y., 1989), and other suitable laboratory manuals.

Two useful approaches are electroporation and lipofection. Brief examples of each are described below.

The DNA construct can be stably introduced into a donor somatic cell line by electroporation using the following protocol: somatic cells, e.g., fibroblasts, e.g., embryonic fibroblasts, are resuspended in PBS at about $4 \times 10^6$ cells/ml. Fifty micorgrams of linearized DNA is added to the 0.5 ml cell suspension, and the suspension is placed in a 0.4 cm electrode gap cuvette (Biorad). Electroporation is performed using a Biorad Gene Pulser electroporator with a 330 volt pulse at 25 mA, 1000 microFarad and infinite resistance. If the DNA construct contains a Neomyocin resistance gene for selection, neomyocin resistant clones are selected following incubation with 350 microgram/ml of G418 (GibcoBRL) for 15 days.

The DNA construct can be stably introduced into a donor somatic cell line by lipofection using a protocol such as the following: about $2 \times 10^5$ cells are plated into a 3.5 cmiameter well and transfected with 2 micrograms of linearized DNA using LipfectAMINE™ (GibcoBRL). Forty-eight hours after transfection, the cells are split 1:1000 and 1:5000 and, if the DNA construct contains a neomyosin resistance gene for selection, G418 is added to a final concentration of 0.35 mg/ml. Neomyocin resistant clones are isolated and expanded for cyropreservation as well as nuclear transfer.

Tissue-Specific Expression of Proteins

It is often desirable to express a protein, e.g., a heterologous protein, in a specific tissue or fluid, e.g., the milk, of a transgenic animal. The heterologous protein can be recovered from the tissue or fluid in which it is expressed. For example, it is often desirable to express the heterologous protein in milk. Methods for producing a heterologous protein under the control of a milk specific promoter are described below. In addition, other tissue-specific promoters, as well as, other regulatory elements, e.g., signal sequences and sequence which enhance secretion of non-secreted proteins, are described below.

Milk Specific Promoters

Useful transcriptional promoters are those promoters that are preferentially activated in mammary epithelial cells, including promoters that control the genes encoding milk proteins such as caseins, beta lactoglobulin (Clark et al., (1989) Bio/Technology 7: 487–492), whey acid protein (Gordon et al. (1987) Bio/Technology 5: 1183–1187), and lactalbumin (Soulier et al., (1992) FEBS Letts. 297: 13). Casein promoters may be derived from the alpha, beta, gamma or kappa casein genes of any mammalian species; a preferred promoter is derived from the goat beta casein gene (DiTullio, (1992) Bio/Technology 10:74–77). Milk-specific protein promoter or the promoters that are specifically activated in mammary tissue can be derived from cDNA or genomic sequences. Preferably, they are genomic in origin.

DNA sequence information is available for the mammary gland specific genes listed above, in at least one, and often in several organisms. See, e.g., Richards et al., J. Biol. Chem. 256, 526–532 (1981) ($\alpha$-lactalbumin rat); Campbell et al., Nucleic Acids Res. 12, 8685–8697 (1984) (rat WAP); Jones et al., J. Biol. Chem. 260, 7042–7050 (1985) (rat $\beta$-casein); Yu-Lee & Rosen, J. Biol. Chem. 258, 10794–10804 (1983) (rat $\gamma$-casein); Hall, Biochem. J. 242, 735–742 (1987) ($\alpha$-lactalbumin human); Stewart, Nucleic Acids Res. 12, 389 (1984) (bovine $\alpha s1$ and $\kappa$ casein cDNAs); Gorodetsky et al., Gene 66, 87–96 (1988) (bovine $\beta$ casein); Alexander et al., Eur. J. Biochem. 178, 395–401 (1988) (bovine $\kappa$ casein); Brignon et al., FEBS Lett. 188, 48–55 (1977) (bovine $\alpha S2$ casein); Jamieson et al., Gene 61, 85–90 (1987), Ivanov et al., Biol. Chem. Hoppe-Seyler 369, 425–429 (1988), Alexander et al., Nucleic Acids Res. 17, 6739 (1989) (bovine $\beta$ lactoglobulin); Vilotte et al., Biochimie 69, 609–620 (1987) (bovine $\alpha$-lactalbumin). The structure and function of the various milk protein genes are reviewed by Mercier & Vilotte, J. Dairy Sci. 76, 3079–3098 (1993) (incorporated by reference in its entirety for all purposes). If additional flanking sequence are useful in optimizing expression of the heterologous protein, such sequences can be cloned using the existing sequences as probes. Mammary-gland specific regulatory sequences from different organisms can be obtained by screening libraries from such organisms using known cognate nucleotide sequences, or antibodies to cognate proteins as probes.

Signal Sequences

Useful signal sequences are milk-specific signal sequences or other signal sequences which result in the secretion of eukaryotic or prokaryotic proteins. Preferably, the signal sequence is selected from milk-specific signal sequences, i.e., it is from a gene which encodes a product secreted into milk. Most preferably, the milk-specific signal sequence is related to the milk-specific promoter used in the construct, which are described below. The size of the signal sequence is not critical. All that is required is that the sequence be of a sufficient size to effect secretion of the desired recombinant protein, e.g., in the mammary tissue. For example, signal sequences from genes coding for caseins, e.g., alpha, beta, gamma or kappa caseins, beta lactoglobulin, whey acid protein, and lactalbumin can be used. A preferred signal sequence is the goat $\beta$-casein signal sequence.

Signal sequences from other secreted proteins, e.g., proteins secreted by kidney cells, pancreatic cells or liver cells, can also be used. Preferably, the signal sequence results in the secretion of proteins into, for example, urine or blood.

Amino-Terminal Regions of Secreted Proteins

A non-secreted protein can also be modified in such a manner that it is secreted such as by inclusion in the protein to be secreted of all or part of the coding sequence of a protein which is normally secreted. Preferably the entire sequence of the protein which is normally secreted is not included in the sequence of the protein but rather only a sufficient portion of the amino terminal end of the protein which is normally secreted to result in secretion of the protein. For example, a protein which is not normally secreted is fused (usually at its amino terminal end) to an amino terminal portion of a protein which is normally secreted.

In one aspect, the protein which is normally secreted is a protein which is normally secreted in milk. Such proteins include proteins secreted by mammary epithelial cells, milk proteins such as caseins, beta lactoglobulin, whey acid protein, and lactalbumin. Casein proteins include alpha, beta, gamma or kappa casein genes of any mammalian species. A preferred protein is beta casein, e.g., goat beta casein. The sequences which encode the secreted protein can be derived from either cDNA or genomic sequences. Preferably, they are genomic in origin, and include one or more introns.

Other Tissue-Specific Promoters

Other tissue-specific promoters which provide expression in a particular tissue can be used. Tissue specific promoters are promoters which are expressed more strongly in a particular tissue than in others. Tissue specific promoters are often expressed essentially exclusively in the specific tissue.

Tissue-specific promoters which can be used include: a neural-specific promoter, e.g., nestin, Wnt-1, Pax-1, Engrailed-1, Engrailed-2, Sonic hedgehog; a liver-specific promoter, e.g., albumin, alpha-1 antirypsin; a muscle-specific promoter, e.g., myogenin, actin, MyoD, myosin; an oocyte specific promoter, e.g., ZP1, ZP2, ZP3; a testes-specific promoter, e.g., protamin, fertilin, synaptonemal complex protein-1; a blood-specific promoter, e.g., globulin, GATA-1, porphobilinogen deaminase; a lung-specific promoter, e.g., surfactant protein C; a skin- or wool-specific promoter, e.g., keratin, elastin; endothelium-specific promoters, e.g., Tie-1, Tie-2; and a bone-specific promoter, e.g., BMP.

In addition, general promoters can be used for expression in several tissues. Examples of general promoters include β-actin, ROSA-21, PGK, FOS, c-myc, Jun-A, and Jun-B.

DNA Constructs

A cassette which encodes a heterologous protein can be assembled as a construct which includes a promoter for a specific tissue, e.g., for mammary epithelial cells, e.g., a casein promoter, e.g., a goat beta casein promoter, a milk-specific signal sequence, e.g., a casein signal sequence, e.g., a β-casein signal sequence, and a DNA encoding the heterologous protein.

The construct can also include a 3' untranslated region downstream of the DNA sequence coding for the non-secreted protein. Such regions can stabilize the RNA transcript of the expression system and thus increases the yield of desired protein from the expression system. Among the 3' untranslated regions useful in the constructs for use in the invention are sequences that provide a poly A signal. Such sequences may be derived, e.g., from the SV40 small t antigen, the casein 3' untranslated region or other 3' untranslated sequences well known in the art. In one aspect, the 3' untranslated region is derived from a milk specific protein. The length of the 3' untranslated region is not critical but the stabilizing effect of its poly A transcript appears important in stabilizing the RNA of the expression sequence.

Optionally, the construct can include a 5' untranslated region between the promoter and the DNA sequence encoding the signal sequence. Such untranslated regions can be from the same control region from which promoter is taken or can be from a different gene, e.g., they may be derived from other synthetic, semi-synthetic or natural sources. Again their specific length is not critical, however, they appear to be useful in improving the level of expression.

The construct can also include about 10%, 20%, 30%, or more of the N-terminal coding region of a gene preferentially expressed in mammary epithelial cells. For example, the N-terminal coding region can correspond to the promoter used, e.g., a goat β-casein N-terminal coding region.

The construct can be prepared using methods known in the art. The construct can be prepared as part of a larger plasmid. Such preparation allows the cloning and selection of the correct constructions in an efficient manner. The construct can be located between convenient restriction sites on the plasmid so that they can be easily isolated from the remaining plasmid sequences for incorporation into the desired mammal.

Heterologous Proteins

Transgenic sequences encoding heterologous proteins can be introduced into the germline of a non-human mammal or can be transfected into a cell line to provide a source of genetically engineered somatic cells as described above. The protein can be a complex or multimeric protein, e.g., a homo- or heteromultimer, e.g., proteins which naturally occur as homo- or heteromultimers, e.g., homo- or heterodimers, trimers or tetramers. The protein can be a protein which is processed by removal, e.g., cleavage, of N-terminus, C-terminus or internal fragments. Even complex proteins can be expressed in active form. Protein encoding sequences which can be introduced into the genome of mammal, e.g., goats, include glycoproteins, neuropeptides, immunoglobulins, enzymes, peptides and hormones. The protein may be a naturally occurring protein or a recombinant protein, e.g., a fragment, fusion protein, e.g., an immunoglogulin fusion protein, or mutien. It may be human or non-human in origin. The heterologous protein may be a potential therapeutic or pharmaceutical agent such as, but not limited to: alpha-1 proteinase inhibitor, alpha-1 antitrypsine, alkaline phosphatase, angiogenin, antithrombin III, any of the blood clotting factors including Factor VIII, Factor IX, and Factor X chitinase, erythropoietin, extracellular superoxide dismutase, fibrinogen, glucocerebrosidase, glutamate decarboxylase, human growth factor, human serum albumin, immunoglobulin, insulin, myelin basic protein, proinsulin, prolactin, soluble CD4 or a component or complex thereof, lactoferrin, lactoglobulin, lysozyme, lactalbumin, tissue plasminogen activator or a variant thereof.

Immunoglobulins are particularly preferred heterologous protiens. Examples of immunoglobulins include IgA, IgG, IgE, IgM, chimeric antibodies, humanized antibodies, recombinant antibodies, single chain antibodies and antibody-protein fusions.

Nucleotide sequence information is available for several of the genes encoding the heterologous proteins listed above, in at least one, and often in several organisms. See e.g., Long et al. (1984) *Biochem.* 23(21):4828–4837 (aplha-1 antitrypsin); Mitchell et al. (1986) *Prot. Natl. Acad.*

Sci USA 83:7182–7186 (alkaline phosphatase); Schneider et al. (1988) *EMBO J.* 7(13):4151–4156 (angiogenin); Bock et al. (1988) *Biochem.* 27(16):6171–6178 (antithrombin III); Olds et al. (1991) *Br. J. Haematol.* 78(3):408–413 (antithrombin III); Lin et al. (1985) *Proc. Natl. Acad. Sci. USA* 82(22):7580–7584 (erythropoeitin); U.S. Pat. No. 5,614,184 (erythropoietin); Horowitz et al. (1989) *Genomics* 4(1):87–96 (glucocerebrosidase); Kelly et al. (1992) *Ann. Hum. Genet.* 56(3):255–265 (glutamte decarboxylase); U.S. Pat. No. 5,707,828 (human serum albumin); U.S. Pat. No. 5,652,352 (human serum albumin); Lawn et al. (1981) *Nucleic Acid Res.* 9(22):6103–6114 (human serum albumin); Kamholz et al. (1986) *Prot. Natl. Acad. Sci. USA* 83(13):4962–4966 (myelin basic protein); Hiraoka et al. (1991) *Mol. Cell Endocrinol.* 75(1):71–80 (prolactin); U.S. Pat. No. 5,571,896 (lactoferrin); Pennica et al. (1983) *Nature* 301(5897):214–221 (tissue plasminogen activator); Sarafanov et al. (1995) *Mol. Biol.* 29:161–165, the contents of which are incorporated herein by reference.

Oocytes

Suitable sources of oocytes include goat, cow, sheep, horse, pig, llama, camel, etc. Preferably the oocyte is obtained from a goat. Oocytes for use in the invention include oocytes in metaphase II stage, e.g., oocytes arrested in metaphase II, and telophase II. Oocytes in metaphase II contain one polar body, whereas oocytes in telophase can be identified based on the presence of a protrusion of the plasma membrane from the second polar body up to the formation of a second polar body. In addition, oocytes in metaphase II can be distinguished from oocytes in telophase II based on biochemical and/or developmental distinctions. For example, oocytes in metaphase II can be in an arrested state, whereas oocytes in telophase are in an activated state.

Occytes can be obtained at various times during a goat's reproductive cycle. For example, at given times during the reproductive cycle, a significant percentage of the oocytes, e.g., about 55%, 60%, 65%, 70%, 75%, 80% or more, are oocytes in telophase. In addition, oocytes at various stages of the cell cycle can be obtained and then induced in vitro to enter a particular stage of meiosis. For example, oocytes cultured on serum-starved medium become arrested in metaphase. In addition, arrested oocytes can be induced to enter telophase by serum activation. Thus, oocytes in telophase can be easily obtained for use in the invention. Thus, oocytes can be matured in vitro before they are used to form a reconstructed embryo. This process usually requires collecting immature oocytes from mammalian ovaries, e.g., a caprine ovary, and maturing the oocyte in a medium prior to enucleation until the oocyte reaches the desired meiotic stage, e.g., metaphase or telophase. In addition, oocytes that have been matured in vivo can be used to form a reconstructed embryo.

Oocytes can be collected from a female mammal during superovulation. Briefly, oocytes, e.g., caprine oocytes, can be recovered surgically by flushing the oocytes from the oviduct of the female donor. Methods of inducing superovulation in goats and the collection of caprine oocytes is described herein.

Preferably, the mitotic stage of the oocyte, e.g., metaphase II or telophase II, correlates to the stage of the cell cycle of the donor somatic cell. The correlation between the meiotic stage of the oocyte and the mitotic stage of the cell cycle of the donor somatic cell is referred to herein as "synchronization". For example, reconstruction of an oocyte in metaphase II by introduction of a nucleus of a somatic cell in $G_0$ or $G_1$, e.g., by simultaneous activation and fusion, can mimic the events occurring during fertilization. By way of another example, an oocyte in telophase fused, e.g., by simultaneous activation and fusion, with the genome of a somatic cell in $G_1$ prior to START, provides a synchronization between the oocyte and the donor nuclei.

Functional Enucleation

The donor oocyte, e.g., caprine oocyte, should be functionally enucleated such that the endogenous genome of the oocyte is incapable of functioning, e.g., replicating or synthesizing DNA. Methods of functionally enucleating an oocyte include: removing the genome from the oocyte (i.e., enucleation); inactivating DNA within the oocyte, e.g., by irradiation (e.g., by X-ray irradiation, or laser irradiation); chemical inactivation, or the like.

Enucleation

One method of rendering the genome of an oocyte incapable of functioning is to remove the genome from the oocyte (i.e., enucleation). A micropipette or needle can be inserted into the zona pellicuda in order to remove nuclear material from an oocyte. For example, metaphase II stage oocytes which have one polar body can be enucleated with a micropipette by aspirating the first polar body and adjacent cytoplasm surrounding the polar body, e.g., approximately 20%, 30%, 40%, 50%, 60% of the cytoplasm, which presumably contains the metaphase plate. Telphase stage oocytes which have two polar bodies can be enucleated with a micropipette or needle by removing the second polar body and surrounding cytoplasm, e.g., approximately 5%, 10%, 20%, 30%, 40%, 50%, 60% of cytoplasm. Specifically, oocytes in telophase stage can be enucleated at any point from the presence of a protrusion in the plasma membrane from the second polar body up to the formation of the second polar body. Thus, as used herein, oocytes which demonstrate a protrusion in the plasma membrane, usually with a spindle abutted to it, up to extrusion of the second polar body are considered to be oocytes in telophase. Alternatively, oocytes which have one clear and distinct polar body with no evidence of protrusion are considered to be oocytes in metaphase. Methods of enucleating an oocyte, e.g., a caprine oocyte, are described in further detail in the Examples.

Irradiation

The oocyte can be functionally enucleated by inactivating the endogenous DNA of the oocyte using irradiation. Methods of using irradiation are known in the art and described, for example, in Bradshaw et al. (1995) *Molecul. Reprod. Dev.* 41:503–512, the contents of which is incorporated herein by reference.

Chemical Inactivation

The oocyte can be functionally enucleated by chemically inactivating the endogenous DNA of the oocyte. Methods of chemically inactivating the DNA are known in the art. For example, chemical inactivation can be performed using the etopsoide-cycloheximide method as described in Fulkaj and Moore (1993) *Molecul. Reprod. Dev.* 34:427–430, the content of which are incorporated herein by reference.

Introduction of a Functional Chromosomal Genome Into an Oocyte

Methods described herein can include the introduction of a functional chromosomal genome into an oocyte, e.g., a functionally enucleated oocyte, e.g., an enucleated oocyte, to form a reconstructed embryo. The functional chromosomal genome directs the development of a cloned or transgenic animal which arises from the reconstructed embryo. Methods which result in the transfer of an essentially intact chromosomal genome to the oocyte can be used. Examples include fusion of a cell which contains the functional chromosomal genome with the oocyte and nuclear injection, i.e., direct transfer of the nucleus into the oocyte.

Fusion

Fusion of the somatic cell with an oocyte can be performed by, for example, electrofusion, viral fusion, biochemical reagent fusion (e.g., HA protein), or chemical fusion (e.g., with polyethylene glycol (PEG) or ethanol).

Fusion of the somatic cell with the oocyte and activation can be performed simultaneously. For example, the nucleus of the somatic cell can be deposited within the zona pelliduca which contains the oocyte. The steps of fusing the nucleus with the oocyte and activation can then be performed simultaneously by, for example, applying an electric field. Methods of simultaneous fusion and activation of a somatic cell and an oocyte are described herein.

Activation of a Recombinant Embryo

Activation refers to the beginning of embryonic development, e.g., replication and DNA synthesis. Activation can be induced by, for example, electric shock (e.g., in electrofusion), the use of ionophores, ethanol activation, or the oocyte can be obtained during a stage in which it is naturally activated, e.g., an oocyte in telophase.

Electrofusion

A reconstructed embryo can be activated using electric shock, i.e., electrofusion. The use of electrofusion allows for the fusion of the somatic cell with the oocyte and activation to be performed simultaneously.

Chambers, such as the BTX 200 Embryomanipulation System, for carrying out electrofusion are commercially available from, for example, BTX, San Diego. Methods for performing electrofusion to fuse a somatic cell, e.g., a caprine somatic cell, and an oocyte, e.g., an enucleated oocyte, e.g., an enucleated caprine oocyte, are described herein.

Ionophores

In addition, the reconstructed embryo can be activated by ionophore activation. Using an ionophore, e.g., a calcium ionophore, the calcium concentration across the membrane of the reconstructed embryo is changed. As the free calcium concentration in the cell increases, there is a decrease in phosphorylation of intracellular proteins and the oocyte is activated. Such methods of activation are described, for example, in U.S. Pat. No. 5,496,720, the contents of which are incorporated by reference.

Ethanol Activation

Prior to enucleation, an oocyte, e.g., an oocyte in metaphase II, can be activated with ethanol according to the ethanol activation treatment as described in Presicce and Yang (1994) *Mol. Reprod. Dev.* 37:61–68, and Bordignon and Smith (1998) *Mol. Reprod. Dev.* 49:29–36, the contents of which are incorporated herein by reference.

Ooctyes in Telophase

Oocytes in telophase are generally already activated. Thus, these cells often naturally exhibit a decrease in calcium concentration which prevents fertilization and allows the embryo to develop.

Transfer of Reconstructed Embryos

A reconstructed embryo of the invention can be transferred to a recipient doe and allowed to develop into a cloned or transgenic mammal, e.g., a cloned or transgenic goat. For example, the reconstructed embryo can be transferred via the fimbria into the oviductal lumen of each recipient doe as described below in the Examples. In addition, methods of transferring an embryo to a recipient mammal are known in the art and described, for example, in Ebert et al. (1994) *Bio/Technology* 12:699.

The reconstructed embryo can be maintained in a culture until at least first cleavage (2-cell stage) up to the eight cell-stage of embryogenesis, preferably the embryos are transferred at 2-cell or 4 cell-stage. Various culture media for embryo development are known in the art. For example, the reconstructed embryo can be co-cultured with oviductal epithelial cell monolayer derived from the type of mammal to be provided by the invention. Methods of obtaining goat oviductal epithelial cells (GOEC), maintaining the cells in a co-culture are described in the Examples below.

EXAMPLES

Donors and recipients used in the following examples were dairy goats of the following breeds (mixed or not): Alpine, Saanen, and Toggenburg. All goats were maintained at the Genzyme Transgenics farm in Charlton, Mass. Collections and transfers were completed during the spring and early summer (off-season).

Isolation of Caprine Somatic Cells

Caprine fetal fibroblast cell lines used as karyoplast donors were derived from six day 35–40 fetuses produced by artificially inseminating non-transgenic does with fresh collected semen from a transgenic antithrombin III (ATIII) founder buck. An ATIII cell line was chosen since it provides a well characterized genetic marker to the somatic cell lines, and it targets high level expression of a complex glycosylated protein (ATIII) in the milk of lactating does. Three fetuses which were derived from the semen of the transgenic ATIII buck were surgically removed at day 40 post coitus and placed in equilibrated $Ca^{++}/Mg^{++}$-free phosphate buffered saline (PBS). Cell suspensions were prepared by mincing and digesting fetal tissue in 0.025% trypsin/0.5 mM EDTA at 37° C. for ten minutes. Cells were washed with equilbrated Medium 199™ (M199)(Gibco)+10% Fetal Bovine Serum (FBS) supplemented with nucleosides, 0.1 mM 2-mercaptoethanol, 2 mM L-glutamine, 1% penicillin/streptomycin (10,000 I.U. each/ml) (fetal cell medium), and cultured in 25 cm$^2$ flasks. The cultures were re-fed 24 hours later with equilibrated fetal cell medium. A confluent monolayer of primary fetal cells was harvested by trypsinization on day four by washing the monolayer twice with $Ca^{++}/Mg^{++}$-free PBS, followed by incubation with 0.025% trypsin/0.5 mM EDTA at 38° C. for 7 minutes.

Cells potentially expressing ATIII were then prepared for cryopreservation, or maintained as stock cultures.

Sexing and Genotyping of Donor Cell Lines

Genomic DNA was isolated from fetal head tissue for ATIII donor karyoplasts by digestion with proteinase K followed by precipitation with isopropanol as described in Laird et al. (1991) *Nucleic Acid Res.* 19:4293, and analyzed by polymerase chain reaction (PCR) for the presence of human Antithrombin III (ATIII) sequences as well as for sexing. The ATIII sequence is part of the BC6 construct (Goat Beta-Casein—human ATIII cDNA) used to generate the ATIII transgenic line as described in Edmunds et al. (1998) *Blood* 91:4561–4571. The human ATIII sequence was detected by amplification of a 367 bp sequence with oligonucleotides GTC11 and GTC12 (see below). For sexing, the zfX/zfY primer pair was used (see below) giving rise to a 445 bp (zfX)/447 bp (zfy) doublet. Upon digestion with the restriction enzyme SacI (New England Biolabs), the zfX band was cut into two small fragments (272 and 173 bp). Males were identified by the presence of the uncut 447 bp zfY band.

For the PCR reactions, approximately 250 ng of genomic DNA was diluted in 50 ml of PCR buffer (20 mM Tris pH 8.3, 50 mM KCl and 1.5 mM $MgCl_2$, 0.25 mM deoxynucleotide triphosphates, and each primer at a concentration of 600 mM) with 2.5 units of Taq polymerase and processed using the following temperature program:

| 1 cycle at | 94° C. | 60 seconds | |
|---|---|---|---|
| 5 cycles at | 94° C. | 30 seconds | |
| | | 58° C. | 45 seconds |
| | | 74° C. | 45 seconds |
| 30 cycles at | 94° C. | 30 seconds | |
| | | 55° C. | 30 seconds |
| | | 74° C. | 30 seconds |

The following primer set was used to detect the human ATIII sequence:
GTC 11: CTCCATCAGTTGCTGGAGGGTGTCATTA (SEQ ID NO:1)
GTC 12: GAAGGTTTATCTTTTGTCCTTGCTGCTCA (SEQ ID NO:2)
The following primer set was used for sexing:
zfX: ATAATCACATGGAGAGCCACAAGC (SEQ ID NO:3)
zfY: GCACTTCTTTGGTATCTGAGAAAG (SEQ ID NO:4)

Two of the fetuses were identified to be male and were both negative for the ATIII sequence. Another fetus was identified as female and confirmed positive for the presence of the ATIII sequence.

Preparation of ATIII-Expressing Donor Cells for Embryo Reconstitution

A transgenic female line (CFF155-92-6) originating from a day 40 fetus was identified by PCR analyses, as described above, and used for all nuclear transfer manipulations. Transgenic fetal fibroblast cells were maintained in 25 cm² flasks with fetal cell medium, re-fed on day four following each passage, and harvested by trypsinization on day seven. From each passage, a new 25 cm² flasks was seeded to maintain the stock culture. Briefly, fetal cells were seeded in 4-well plates with fetal cell medium and maintained in culture (5% $CO_2$ at 39° C.). Forty-eight hours later, the medium was replaced with fresh fetal cell medium containing 0.5% FBS. The culture was re-fed every 48–72 hours over the next seven days with fresh fetal cell medium containing 0.5% FBS. On the seventh day following first addition of fetal cell medium (0.5% FBS), somatic cells used as karyoplast donors were harvested by trypsinization as previously described. The cells were resuspended in equilibrated M199+10% FBS supplemented with 2 mM L-glutamine, 1% penicillin/streptomycin (10,000 I.U. each/ ml) one to three hours prior to fusion to the enucleated oocytes.

Karyotyping of Cell Lines

The clonal lines were further evaluated by karyotyping to determine gross chromosomal abnormalities in the cell lines. Cells were induced to arrest at metaphase by incubation with 0.02 µg/ml of Demecolcine (Sigma) for 12 hours. After trypsinization, the resulting pellet was suspended in a hypotonic solution of 75 mM KCl in water and incubated at 37° C. for 20 minutes. Cells were fixed for 5 minutes each time in 3 changes of ice-cold acetic acid-methanol (1:3) solution before drops of the cell suspension were placed in pre-washed microscopic slides. Following air-drying, chromosome preparations were stained with 3% Giemsa stain (Sigma) in PBS for 10 minutes. The chromosome spreads were counted for each cell line at 1000× magnification under oil immersion.

Immunohistochemical Analysis

Antibodies specific for vimentin (Sigma) and pan-cytokeratin (Sigma) were used to characterize and confirm the morphology of the cell lines. Cells were plated in sterile gelatin coated cover slips to 75% confluency and fixed in 2% paraformaldehyde with 0.05% saponin for 1 hour. Cells were incubated in 0.5% PVP in PBS (PBS/PVP) with primary antibodies for 2 hours at 37° C., rinsed with 3 changes of PBS/PVP at 10 minute intervals, and incubated for 1 hour in secondary antibodies conjugated with Cy3 and FITC respectively. Alkaline phosphatase (Sigma) activity of the cells was also performed to determine the presence or absence of undifferentiated cells, The cover slips were rinsed and subsequently mounted on glass slides with 50% glycerol inPBS/PVP with 10 µg/ml bisbenzimide (H-33342, Sigma) and observed under fluorescent microscopy.

Epithelial and fibroblast lines positive for vimentin and pan-cytokeratin, respectively, and negative for alkaline phosphatase activity were generated from the ATIII primary cultures. In the cell cultures, two morphologically distinct cell types were observed. Larger "fibroblast-like" cells stained positive for vimentin and smaller "epithelial-like" cells stained positive for pan-cytokeratin which coexisted in the primary cell cultures. The isolated fibroblast lines from ATIII showed a tendency to differentiate into epithelial-like cells when cultured for 3 days after reaching confluency. Subsequent passages induced selection against fibroblast cells giving rise to pure epithelial cells as confirmed by the lack of positive staining for vimentin. Senesces or possible cell cycle arrest was first observed at passage 28. These cells appear bigger in size (>30 µm) compared to the normally growing cells (15–25 µm) and can be maintained in culture in the absence of apparent mitotic activity for several months without loss of viability. Embryo reconstruction using nuclei from the arrested cells produced morula stage embyos suggesting reacquistion of mitotic activity.

Superovulation of Donor Goats and Oocyte Collection

Estrus was synchronized on day 0 by a 6 mg subcutaneous Norgestomet ear implant (Synchro-mate B). A single injection of prostaglandin (PGF2α)(Upjohn US) was administered on day 7. Starting on day 12, FSH (Folltropin-V, Vetrepharm, St Laurent, Quebec, Canada) was administered twice daily over four consecutive days. The ear implant was removed on day 14. Twenty-four hours following implant removal, the donor animals were mated several times to vasectomized males over a 48 hour interval. A single injection of GnRH (Rhone-Merieux US) was administered intramuscularly following the last FSH injection. Oocytes were recovered surgically from donor animals by mid-ventral laparotomy approximately 18 to 24 hours following the last mating, by flushing the oviduct with $Ca^{++}/Mg^{++}$-free PBS prewarmed at 37° C. Oocytes were then recovered and cultured in equilibrated M199+10%FBS supplemented with 2 mM L-glutamine, 1% penicillin/streptomycin (10,000 I.U. each/ml).

Oocyte Enucleation

In vivo matured oocytes were collected from donor goats. Oocytes with attached cumulus cells or devoid of polar bodies were discarded. Cumulus-free oocytes were divided into two groups: oocytes with only one polar body evident (metaphase II stage) and the activated telophase II protocol (oocytes with one polar body and evidence of an extruding second polar body). Oocytes in telophase II were cultured in M199+10% FBS for 2 to 4 hours. Oocytes that had activated during this period, as evidenced by a first polar body and a partially extruded second polar body, were grouped as culture induced, calcium activated telophase II oocytes (Telophase II-$Ca^{2+}$) and enucleated. Oocytes that had not activated were incubated for 5 minutes in PBS containing 7% ethanol prior to enucleation. Metaphase II stage oocytes (one polar body) were enucleated with a 25–30 micron glass pipette by aspirating the first polar body and adjacent cytoplasm surrounding the polar body (approximately 30% of the cytoplasm) presumably containing metaphase plate.

As discussed above, telophase stage oocytes were prepared by two procedures. Oocytes were intially incubated in phosphate buffered saline (PBS, $Ca^{2+}/Mg^{2+}$ free) supplemented with 5% FBS for 15 minutes and cultured in M199+10% FBS at 38° C. for approximately three hours until the telophase spindle configuration or the extrusion of the second polar body was reached. All the oocytes that responded to the sequential culture under differential extracellular calcium concentration treatment were seperated and grouped as Telophase II-$Ca^{2+}$. The other oocytes that did not respond were further incubated in 7% ethanol in M199+10% FBS for 5–7 minutes (Telophase II-ETOH) and cultured in M199+10% FBS at 38° C. for another 3 hours until the telophase II spindle configuration was reached. Thereafter, the oocytes were incubated in 30–50 $\mu$l drops of M199+10% FBS containing 5 $\mu$g/ml of cytochalasin-B for 10–15 minutes at 38° C. Oocytes were enucleated with a 30 micron (OD) glass pipette by aspirating the first polar body and approximately 30% of the adjacent cytoplasm containing the metaphase II or about 10% of the cytoplasm containing the telophase II spindle. After enucleation the oocytes were immediately reconstructed.

Embryo Reconstruction

CFF155-92-6 somatic cells used as karyoplast donors were harvested on day 7 by trypsinizing (0.025% trypsin/0.5 mM EDTA)(Sigma) for 7 minutes. Single cells were resuspended in equilibrated M199+10% FBS supplemented with 2 mM L-glutamine, penicillin/streptomycin. The donor cell injection was carried out in the same medium as for enucleation. Donor cells were graded into small, medium and large before selection for injection to enucleated cytoplasts. Small single cells (10–15 micron) were selected with a 20–30 micron diameter glass pipette. The pipette was introduced through the same slit of the zona made during enucleation and donor cells were injected between the zona pellucida and the ooplasmic membrane. The reconstructed embryos were incubated in M199 30–60 minutes before fusion and activation.

Fusion and Activation

All reconstructed embryos (ethanol pretreatment or not) were washed in fusion buffer (0.3 M mannitol, 0.05 mM $CaCl_2$, 0.1 mM $MgSO_4$, 1 mM $K_2HPO_4$, 0.1 mM glutathione, 0.1 mg/ml BSA in distilled water) for 2 minutes before electrofusion. Fusion and activation were carried out at room temperature, in a chamber with two stainless steel electrodes 200 microns apart (BTX 200 Embryomanipulation System, BTX-Genetronics, San Diego, Calif.) filled with fusion buffer. Reconstructed embryos were placed with a pipette in groups of 3–4 and manually aligned so the cytoplasmic membrane of the recipient oocytes and donor CFF155-92-6 cells were parallel to the electrodes. Cell fusion and activation were simultaneously induced 32–42 hours post GnRH injection with an initial alignment/holding pulse of 5–10 V AC for 7 seconds, followed by a fusion pulse of 1.4 to 1.8 KV/cm DC for 70 microseconds using an Electrocell Manipulator and Enhancer 400 (BTX-Genetronics). Embryos were washed in fusion medium for 3 minutes, then they were transferred to M199 containing 5 $\mu$g/ml cytochalasin-B (Sigma) and 10% FBS and incubated for 1 hour. Embryos were removed from M199/cytochalasin-B medium and cocultured in 50 microliter drops of M199 plus 10% FBS with goat oviductal epithelial cells overlaid with paraffin oil. Embryo cultures were maintained in a humidified 39° C. incubator with 5% $CO_2$ for 48 hours before transfer of the embryos to recipient does.

Reconstructed embryos at 1 hour following simultaneous activation and fusion with $G_0$, $G_1$, and S-phase karyoplasts all showed nuclear envelope breakdown (NEBD) and premature chromosome condensation (PCC) when the cytoplasts were at the arrested metaphase II stage. Subsequent nuclear envelope formation was observed to be at about 35% at 4 hour post activation. Oocytes reconstructed at telophase II stage showed that an average of 22% of oocytes observed at 1 hour post fusion of $G_0$, $G_1$ and S-phase karyoplast underwent NEBD and PCC, whereas the remaining oocytes have intact nuclear lamina surrounding the decondensing nucleus. No consistent nuclear morphology other than lack of, or the occurrence of NEBD and PCC was observed between the metaphase and two telophase reconstruction protocols employed. Differences became evident when cloned embryos were observed to have a higher incidence of advanced cleavage stages (8 to 32 blastomeres) when embryos were reconstructed with S-phase donor nuclei compared to when $G_0$ or $G_1$ stage karyoplasts were used (2 to 8 blastomeres) following culture in vitro for 36 to 48 hours. Fluorescent microscopy analysis showed that the nuclei of some of the rapidly dividing embryos were fragmented. Other embryos developed to the 32 to 64 cell stage within 3 days of culture before cleavage development was blocked. Analysis of blastomere and nuclei numbers of these embryos showed the failure of synchronous occurrence of cytokines and karyokinesis wherein blastomeres were either devoid or their corresponding nuclei or contained multiple nuclei. In contrast, morphologically normal looking embryos showed synchronous cytokinesis and karyokinesis.

Goat Oviductal Epithelial Cells (GOEC)/Reconstructed Embryo Coculture

GOEC were derived from oviductal tissue collected during surgical oviductal flushing performed on synchronized and superovulated does. Oviductal tissue from a single doe was transferred to a sterile 15 ml polypropylene culture tube containing 5 ml of equilibrated M199, 10% FBS, 2 mM L-glutamine, penicillin/strepomycin. A single cell suspension was prepared by vortexing for 1 minute, followed by culture in a humidified 5% CO2 incubator at 38° C. for up to one hour. The tube was vortexed a second time for one minute, then cultured an additional five minutes to allow debris to settle. The top four millimeters containing presumed single cells was transferred to a new 15 ml culture tube and centrifuged at 600×g for 7 minutes, at room temperature. The supernatant was removed, and the cell pellet resuspended in 8 ml of equilibrated GOEC medium. The GOEC were cultured in a 25 $cm^2$ flask, re-fed on day 3, and harvested by trypsinization on day six, as previously described. Monolayers were prepared weekly, from primary GOEC cultures, for each experiment. Cells were resuspended in GOEC medium at $5\times10^5$/ml, and 50 microliter/well was seeded in 4-well plates (15 mm). The medium was overlaid with 0.5 ml light paraffin oil, and the plates were cultured in a humidified 5% $CO^2$ incubator at 38° C. The cultures were re-fed on day two with 80% fresh equilibrated culture medium. All reconstructed embryos were cocultured with the GOEC monolayers in vitro in incubator at 39° C., 5% CO2 before transfer to recipients at GTC farm.

All experimental replicates for ATIII yielded cleavage stage embryos that were transferable on day 2 into synchronized recipients. Embryos using fibroblasts and epithelial cell phenotype as donor karyoplasts showed cleavage and development in culture. The percentage of cleavage development was higher in reconstructed couplets that used preactivated telophase II stage cytoplasts (45%) and telophase II-ethanol activated (56%) when compared to cytoplasts used at metaphase II arrested (35%) using ATIII karyoplasts. There were no differences observed in the cleavage rates of embryos that were reconstructed using donor karyoplasts in $G_0$, $G_1$ or S-phase of the cell cycle although, the morphological quality of embryos was better when donor karyoplasts were in as $G_0$ or $G_1$ compared to S-phase. Embryos were generally between the 2 to 8 cell stage with the majority of the embryos having 3–4 blastomeres at the time of transfer. Normal cleavage development corresponded chronologically to approximately 36 to 48 hours post fusion and activation. Morphologically normal appearing embryos were selected at the 2 to 8 cell stage following development in vitro for 36 to 48 hours.

Estrus Synchronization of Recipient Does

Hormonal treatments were delayed by 1 day for recipients (as compared to donors) to insure donor/recipient synchrony. Estrus was synchronized on day 1 by a 6 mg subcutaneous norgestomet ear implant. A single injection of prostaglandin was administered on day 8. Starting on day 14, a single intramuscular treatment of PMSG (CalBiochem US) was administered. The ear implant was removed on day 15. Twenty-four hours following implant removal, recipient does were mated several times to vasectomized males over three consecutive days.

Embryo Transfer to Recipient Does

Reconstructed embryos were co-cultured with GOEC monolayers for approximately 48 hours prior to transfer to synchronized recipients. Immediately prior to transfer, reconstructed embryos were placed in equilibrated Ham's F-12 medium+10% FBS. Two to four reconstructed embryos were transferred via the fimbria into the oviductal lumen of each recipient. Transfers were performed in a minimal volume of Hams's F-12 medium+10% FBS using a sterile fire-polished glass micropipet.

The development of embryos reconstructed by nuclear transfer using transgenic caprine fetal fibroblasts and in vivo derived oocytes is summarized in Table 1. There was a total of 14 rounds of collection and transfers, with 4 donors set up for collection and 5–6 recipient does set up for transfer 48 hours later. The three different enucleation/activation protocols were employed: Metaphase II, Telophase, and Metaphase II pretreated with Ethanol. Following fusion-activation, reconstructed embryos were co-cultured with primary goat epithelial cells, at least until cleavage (2-cell stage) up to early 16-cell stage; with most embryos being transferred at chronologically correct 2- and 4-cell stages. All transfers were surgical and oviductal, in hormonally synchronized recipients (due to the season). Rates of development were slightly superior when using the Telophase protocol and Ethanol protocol as compared to the Metaphase II protocol. This is partly due to the fact that enucleation of the second polar body seems less traumatic for the oocytes, and partly due to what seems to be higher activation rate for oocytes pretreated with ethanol.

TABLE 1

Development of caprine embryos reconstructed by nuclear transfer of transgenic fetal fibroblasts. Three enucleation/procedure were used: Metaphase II (first polar body enucleation), Telophase (second polar body enucleation), Ethanol (preactivation of Metaphase II stage oocytes by 7% ethanol treatment prior to enucleation). In all cases, concomitant fusion and activation was used.

| Enucleation And activation protocol | Oocytes Reconstructed | Oocytes lysed (%) | Embryos Cleaved (%) | Embryos Transferred |
|---|---|---|---|---|
| Metaphase II | 138 | 67 (48.5) | 48 (35) | 47 |
| Telophase | 92 | 38 (41) | 41 (44) | 38 |
| Ethanol | 55 | 23 (42) | 31 (56) | 27 |

Following embryo transfer, recipient does were examined by ultrasound, as early as day 25. High pregnancy rates ranging from 55–78% for ATIII recipient does were diagnosed. For all three enucleation/activation protocols, it was observed that high proportion of does (65%) appeared positive at day 30. However, it must be noted that, in most cases, fetal heartbeats could not be detected at such an early stage. Moreover, the positive ultrasound signal detected at day 30 was not characteristic of normal embryo development and appeared closer to vesicular development not associated with the formation of an embryo proper. This kind of embryonic development is not typically observed in other caprine embryo transfer programs (for example with microinjected embryos). Biweekly, examination of these vesicular developments between day 25 and day 40 established that these pregnancies were abnormal and at day 40, most of the fetuses were reabsorbed and normal ultrasound images were not apparent.

However, for 2 pregnancies, heartbeats were detected by day 40. In these 2 cases, ultrasound examination between day 25 and day 40, not only detected a heartbeat, but also showed the development of recognizable embryonic structures. One of these pregnancies was established using the Metaphase II enucleation/activation protocol, fusing the enucleated cytoplast to a quiescent karyoplast originating from a passage 6 culture of the CFF155-92-6 fibroblast cell line. In this instance, 4 four-cell stage reconstructed embryos were transferred to the oviduct of the recipient doe. The other pregnancy (twins) was obtained from embryos reconstructed according to the Telophase enucleation/activation protocol, fusing an enucleated cytoplast derived from pre-activated telophase $Ca^{2+}$ oocytes and $G_1$ karyoplasts originating from a passage 5 culture of the CFF155-92-6 epithelial cell line. In this case, 3 reconstructed embryos (1 two-cell stage and 2 four-cell stage) were transferred to the oviduct of the recipient doe.

No pregnancies were observed with embryos generated by the Ethanol enucleation/activation protocol. However, numbers are not large enough to conclude on the relative efficacy of the 3 enucleation/activation protocols used in this study.

TABLE 2

Induction of pregnancy and further development following transfer of caprine embryos reconstructed with transgenic fetal fibroblasts and activated according to three protocols

| Enucleation Activation protocol | Recipients (average # of embryos/ recip) | Ultrasound Results (positive/total recip) | | | Term pregnancies |
|---|---|---|---|---|---|
| | | 30 days | 40 days | 50 days | |
| Metaphase II | 15 (3.1) | 9/15 | 1/15 | 1/15 | 1 |
| Telophase | 14 (2.7) | 11/14 | 1/14 | 1/14 | 1 (twins) |
| Ethanol | 9 (3) | 5/9 | 0/9 | 0/9 | 0 |

Perinatal Care of Recipient Embryos

Does were monitored daily throughout pregnancy for outward signs of health (e.g., appetite, alertness, appearance). Pregnancy was determined by ultrasonograph 25–28 days after the first day of standing estrus. Does were ultrasounded biweekly till approximately day 75 and there after once a month to monitor and assess fetal viability. Additionally, recipient does had serum samples drawn at approximately day 21 post standing estrus for serum progesterone analysis. This was to determine if a functioning corpus luteum was present and how this compared to the animal's reproductive status (i.e., pregnancy). At approximately day 130, the pregnant does were vaccinated with tetanus toxoid and Clostridium C&D. Selenium & vitamin E (Bo-Se) and vitamins A, D, and B complex were given intramuscularly or subcutaneously and a dewormer was administered. The does were moved to a clean kidding stall on approximately Day 143 and allowed to acclimate to this new environment prior to kidding. Observations of the pregnant does were increased to monitor for signs of pending parturition. After the beginning of regular contractions, the does remained under periodic observation until birth occurred. If labor was not progressive after approximately 15 minutes of strong contractions the fetal position was assessed by vaginal palpation. If the position appeared normal then the labor was allowed to proceed for an additional 5–30 minutes (depending on the doe) before initiating an assisted vaginal birth. If indicated a cesarean section was performed. When indicated, parturition was induced with approximately 5–10 mg of PGF2α (e.g. Lutalyse). This induction can occur approximately between 145–155 days of gestation. Parturition generally occurs between 30 and 40 hours after the first injection. The monitoring process is the same as described above.

Once a kid was born, the animal was quickly towel dried and checked for gross abnormalities and normal breathing. Kids were immediately removed from the dam. Once the animal was determined to be in good health, the umbilicus was dipped in 7% tincture of iodine. Within the first hour of birth, the kids received their first feeding of heat-treated colostrumn. At the time of birth, kids received injections of selenium & vitamin E (Bo-Se) and vitamins A, D, and B complex to boost performance and health.

The first transgenic female goat offspring was produced by nuclear transfer was born after 154 days of gestation following the induction of parturition and cesarean delivery. The birth weight of the offspring was 2.35 kg which is within the medium weight range of the alpine breed. The female twins were born naturally with minimal assistance a month later with a gestation length of 151 days. The birth weights of the twins were both 3.5 kg which are also within the medium weight range for twins of this breed. All three kids appeared normal and healthy and were phenotypically similar for coat color and expressing markings typical of the alpine breed. In addition, all three offspring were similar in appearance to the transgenic founder buck. No distinguishable phenotypic influence from the breed of the donor oocyte (Saanen, Toggenburg breed) or the heterogeneous expression of the fetal genotype was observed.

All patents and other references cited herein are incorporated by reference. Other embodiments are within the following claims:

What is claimed:

1. A method of producing a cloned goat, comprising:
   maintaining a goat reconstructed embryo, wherein the reconstructed embryo is formed by introduction of an activated cell or cell nucleus into an enucleated oocyte, in culture until the embryo is in the 2 cell stage;
   transferring the goat embryo at the 2 cell stage into a recipient goat; and, allowing the reconstructed embryo to develop into a goat, to thereby produce a cloned goat.

2. The method of claim 1, wherein the cell is a somatic cell.

3. The method of claim 2, wherein the somatic cell is an epithelial cell.

4. The method of claim 2, wherein the somatic cell is a fibroblast.

5. The method of claim 1, wherein the cloned goat is an embryonic goat.

6. The method of claim 1, wherein the cloned goat is a fetal goat.

7. The method of claim 1, wherein the cloned goat is a post natal goat.

8. The method of claim 1 wherein the reconstructed embryo is formed by introduction of a genetically engineered cell or genetically engineered cell nucleus into an enucleated oocyte.

9. The method of claim 8, wherein the genetically engineered cell comprises a trangenic sequence.

10. The method of claim 8, wherein the transgenic goat is an embryonic goat.

11. The method of claim 8, wherein the transgenic goat is a fetal goat.

12. The method of claim 8, wherein the transgenic goat is a post-natal goat.

13. The method of claim 8, wherein the transgenic goat is a female goat.

14. The method of claim 13, wherein the goat can be induced to lactate.

15. The method of claim 9, wherein the transgenic sequence is any of: a heterologous transgene, a knockout, knock in or other event which disrupts the expression of a mammalian gene.

16. The method of claim 9, wherein the transgenic sequence encodes a protein.

17. The method of claim 16, wherein the protein is a human protein.

18. The method of claim 9, wherein the transgenic sequence encodes a protein selected from the group consisting of a hormone, an immunoglobulin, a plasma protein, and an enzyme.

19. The method of claim 9, wherein the transgenic sequence is under the control of a promoter.

20. The method of claim 19, wherein the promoter is a heterologous promoter.

21. The method of claim 20, wherein the milk specific promoter is selected from the group consisting of a casein promoter, a beta lactoglobulin promoter, a whey acid protein promoter and a lactalbumin promoter.

22. The method of claim 19, wherein the promoter is a milk specific promoter.

23. The method of claim 8, wherein a nucleic acid has been introduced into the cell.

24. The method of claim 8, wherein said cell is a fibroblast.

25. A method of producing a cloned goat, comprising:
   maintaining an activated goat reconstructed embryo, wherein the reconstructed embryo is formed by introduction of a cell or cell nucleus into an enucleated oocyte, in culture until the embryo is in the 4 cell stage;
   transferring the goat embryo at the 4 cell stage into a recipient goat; and,
   allowing the reconstructed embryo to develop into a goat, to thereby produce a cloned goat.

26. The method of claim 25, wherein the cell is a somatic cell.

27. The method of claim 26, wherein the somatic cell is an epithelial cell.

28. The method of claim 26, wherein the somatic cell is a fibroblast.

29. The method of claim 25, wherein the cloned goat is an embryonic goat.

30. The method of claim 25, wherein the cloned goat is a fetal goat.

31. The method of claim 25, wherein the cloned goat is a post natal goat.

32. The method of claim 25, wherein the reconstructed embryo is formed by introduction of a genetically engineered cell or genetically engineered cell nucleus into an enucleated oocyte.

33. The method of claim 32, wherein the genetically engineered cell comprises a transgenic sequence.

34. The method of claim 33, wherein the goat is an embryonic goat.

35. The method of claim 33, wherein the goat is a fetal goat.

36. The method of claim 33, wherein the goat is a post-natal goat.

37. The method of claim 33, wherein the goat is a female goat.

38. The method of claim 37, wherein the goat can be induced to lactate.

39. The method of claim 33, wherein the transgenic sequence is any of: a heterologous transgene, a knockout, knockin or other event which disrupts the expression of a mammalian gene.

40. The method of claim 33, wherein the transgenic sequence encodes a protein.

41. The method of claim 40, wherein the protein is a human protein.

42. The method of claim 33, wherein the transgenic sequence encodes a protein selected from the group consisting of a hormone, an immunoglobulin, a plasma protein, and an enzyme.

43. The method of claim 33, wherein the transgenic sequence is under the control of a promoter.

44. The method of claim 43, wherein the promoter is a heterologous promoter.

45. The method of claim 43, wherein the promoter is a milk specific promoter.

46. The method of claim 45, wherein the milk specific promoter is selected from the group consisting of a casein promoter, a beta lactoglobulin promoter, a whey acid protein promoter and a lactalbumin promoter.

47. The method of claim 32, wherein a nucleic acid has been introduced into the cell.

48. A method of producing a cloned goat, comprising:
   maintaining an activated goat reconstructed embryo, wherein the reconstructed embryo is formed by introduction of a cell or cell nucleus into an enucleated oocyte, in culture until the embryo is in the 8 cell stage;
   transferring the goat embryo at the 8 cell stage into a recipient goat; and,
   allowing the reconstructed embryo to develop into a goat, to thereby produce a cloned goat.

49. The method of claim 48, wherein the cloned goat is an embryonic goat.

50. The method of claim 48, wherein the cloned goat is a fetal goat.

51. The method of claim 48, wherein the cloned goat is a post natal goat.

52. The method of claim 48 wherein the reconstructed embryo is formed by introduction of a genetically engineered cell or genetically engineered cell nucleus into an enucleated oocyte.

53. The method of claim 52, wherein the genetically engineered cell comprises a transgenic sequence.

54. The method of claim 52, wherein the goat is an embryonic goat.

55. The method of claim 53, wherein the goat is a fetal goat.

56. The method of claim 53, wherein the goat is a post-natal goat.

57. The method of claim 53, wherein the goat is a female goat.

58. The method of claim 57, wherein the goat can be induced to lactate.

59. The method of claim 53, wherein the transgenic sequence is any of: a heterologous transgene, a knockout, knockin or other event which disrupts the expression of a mammalian gene.

60. The method of claim 53, wherein the transgenic sequence encodes a protein.

61. The method of claim 60, wherein the protein is a human protein.

62. The method of claim 53, wherein the transgenic sequence encodes a protein selected from the group consisting of a hormone, an immunoglobulin, a plasma protein, and an enzyme.

63. The method of claim 53, wherein the transgenic sequence is under the control of a promoter.

64. The method of claim 63, wherein the promoter is a heterologous promoter.

65. The method of claim 63, wherein the promoter is a milk specific promoter.

66. The method of claim 65, wherein the milk specific promoter is selected from the group consisting of a casein promoter, a beta lactoglobulin promoter, a whey acid protein promoter and a lactalbumin promoter.

67. The method of claim 52, wherein a nucleic acid has been introduced into the cell.

68. A kit comprising a goat reconstructed embryo which is in the 2 cell stage.

69. The kit of claim 68, further comprising instructions for producing a goat.

70. A kit comprising a goat reconstructed embryo which is in the 4 cell stage.

71. The kit of claim 70, further comprising instructions for producing a goat.

72. A kit comprising a goat reconstructed embryo which is in the 8 cell stage.

73. The kit of claim 72, further comprising instructions for producing a goat.

* * * * *